US00PP09427P

United States Patent [19]

Jepsen

[11] Patent Number: Plant 9,427

[45] Date of Patent: Jan. 16, 1996

[54] KALANCHOË PLANT NAMED 'ISABELLA'

[75] Inventor: Knud Jepsen, Hinnerup, Denmark

[73] Assignee: Knud Jepsen A/S, Hinnerup, Denmark

[21] Appl. No.: 376,388

[22] Filed: Jan. 23, 1995

[51] Int. Cl.[6] ..... A01H 5/00

[52] U.S. Cl. ..... Plt./87.15

[58] Field of Search ..... Plt./87.15

*Primary Examiner*—James R. Feyrer

*Attorney, Agent, or Firm*—Foley & Lardner

[57] ABSTRACT

A Kalanchoë plant named Isabella particularly characterized by its large and luminous flowers; distinctive and intense petal color; green leaves; and good keeping quality.

1 Drawing Sheet

The present invention relates to a new and distinct cultivar of Kalanchoë plant, botanically known as Kalanchoë, and referred to by the cultivar name Isabella.

The new cultivar was referred to during the breeding and selection process by the designation No. KJ 9/89-11 and is a product of a planned breeding program. The basic objective of the breeding program was to create a new Kalanchoë cultivar having large and luminous flowers, green leaves and a good keeping quality.

The new cultivar was originated from a cross made in a controlled breeding program in Hinnerup, Denmark. The female or seed parent was an undesignated proprietary selection and the male or pollen parent was a cultivar designated Pollux. Isabella was discovered and selected by the inventor, as a flowering plant within the progeny of the stated cross in a controlled environment in Hinnerup, Denmark.

Asexual reproduction of the new cultivar was first accomplished by the inventor in April 1989 in Hinnerup Denmark. Asexual reproduction of the new cultivar by stem cuttings, as performed by the inventor at Hinnerup, Denmark has demonstrated that the combination of characteristics as herein disclosed for the new cultivar are firmly fixed and retained through successive generations of asexual reproduction.

Isabella has not been observed under all possible environmental conditions. The phenotype may vary with variations in environment such as temperature, light intensity and day length without a change in the genotype of the plant. The following observations, measurements and values describe the new cultivar as grown in Hinnerup, Denmark under greenhouse conditions which closely approximate those generally used in commercial practice.

The following traits have been repeatedly observed and are determined to be basic characteristics of Isabella, which in combination, distinguish this Kalanchoë as a new and distinct cultivar:

1. Large and luminous flowers.
2. Distinctive and intense petal color.
3. Green leaves.
4. Good keeping quality.

Isabella is principally distinguished from Pollux by its color and a much longer keeping quality.

The accompanying photographic drawing shows a typical specimen plant of the new cultivar. The colors appearing in the photograph are as true as possible with color illustrations of this type. Photo:

Figure 1:
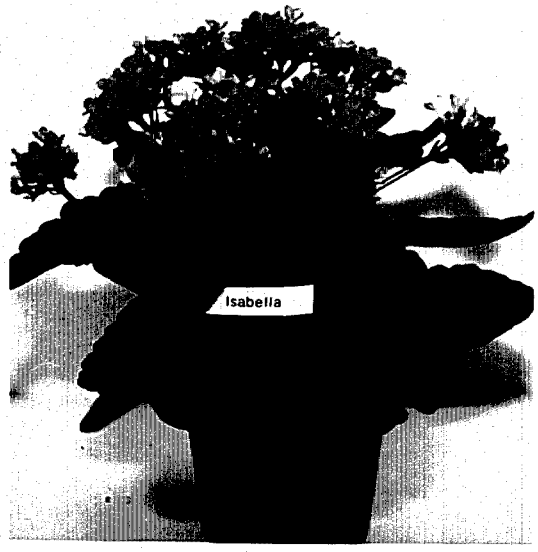
FIG. 1 is a sideview of a typical specimen plant showing the large and luminous flowers.
Figure 2:
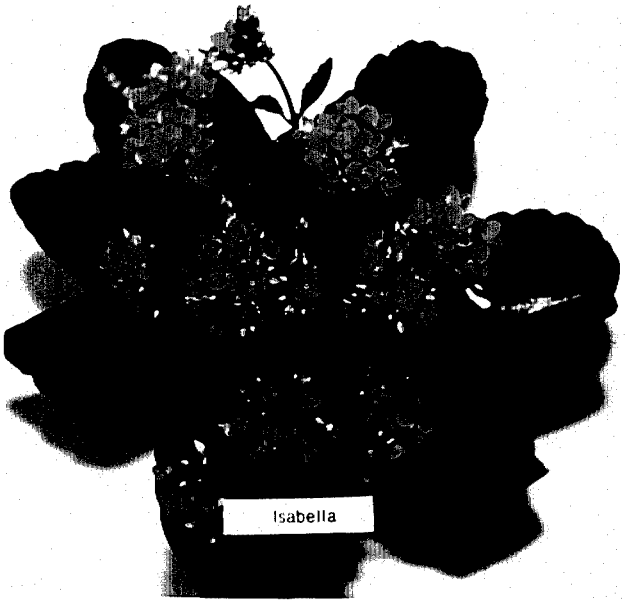
FIG. 2 is a topview of the plant.
Figure 3:
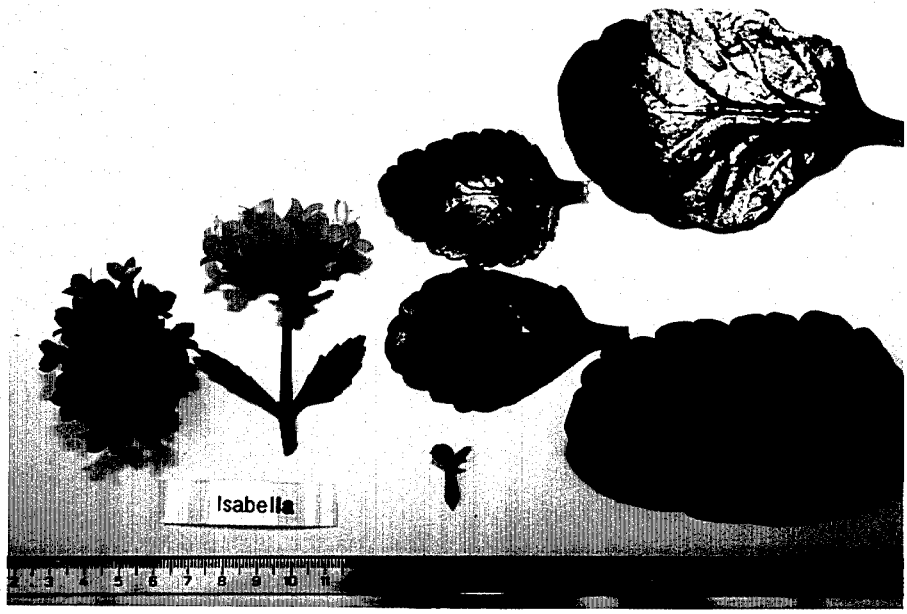
FIG. 3 shows the flowers and leaves in greater detail.

In the following description, color references are made to

The Royal Horticultural Society Colour Chart (RHS), except where general colors of ordinary significance are referred to. Color values were taken under diffuse natural light conditions on a overcast day at 12:00 a.m. in Hinnerup, Denmark.

Botanical classification:

*Commercial.*—*Kalanchoë* cv. Isabella.

Parentage:

*Male parent.*—Pollux.

*Female parent.*—Proprietary and undesignated selection.

Propagation: The new cultivar holds its distinguishing characteristics through successive propagations by leaf cuttings and by division of shoots.

*Type cutting.*—Top shoot.

*Time to root.*—Ten (10) days.

*Rooting habit.*—Branched roots produced from callus.

Plant description:

*Form.*—Compact plant with multiple flowering shoots. Height ca. 25 cm. Diameter ca. 20 cm.

*Habit of growth.*—Upright growth, medium internodes, short and upright flowering shoots.

*Foliage description.*—Medium leaves with short petioles. The leave size is reduced when floral stage is induced. Size: Vegetative leaf is approximately 12 cm× 8 cm. The leaves produced by flowering plants are approximately 7.5 cm×5 cm. Shape: Oval with an obtuse leaf tip. Texture: Glabrous. Margin: Undulate. Color: Young foliage: (topside): RHS 137B. (underside): RHS 137D. Mature foliage: (topside): RHS 139A. (underside): RHS 137B.

Flowering description:

Flowering habits.—Flowering is induced by short day length. Cymes are formed.

*Natural flowering season.*—Winter and spring. Flowering time under controlled day length at 20° C. in summer is eight (8) weeks. In winter (with artificial lighting) at 20° C. the flowering time is nine (9) weeks. Flowering time depends on temperature, light intensity and other growing conditions.

*Flower buds.*—Dusty lilac color. RHS 74B. Size: 1.5 cm×0.3 cm just before anthesis. Shape: Narrow. Rate of opening: 50% open one (1) week after first open flower.

*Flowers borne.*—The flowers are borne in dishasial cymes developing from leaf axils. The main inflorescences are branched into one central and 2–4 minor cymes during development.

*Quantity of flowers.*—8–10 head bunches with 25–45 flowers in 10–20 secondary bunches with 8–12 flowers (unpinched plants).

*Petals.*—Shape: Round obovate with cuspidate leaf tips. Color: Topside when opening: RHS 74A. fading to RHS 74B. Underside: RHS 74C. Number and size of petals: Four (4). Size of flowers: The petals measure 0.9 cm in diameter and the total flower diameter is 1.8 cm.

*Reproductive organs.*— Stamens: Eight (8) in number. Anthers shape: Slightly oblong. Filament color: Yellow/green. Pollen color: Yellow. Pistils: Stigma: Round. Style color: White. Ovaries: Four (4) ovaries each measuring 0.5 cm×0.1 cm. The ovaries are light green and superior (hypogonous).

Disease resistance: No known Kalanchoë diseases observed to date. Resistance not observed.

General observations: Isabella produces high-quality plants without pinching when grown in 9–10 cm pots with one cutting per pot. For larger 12 cm pots high-quality plants are produced when three cuttings or one pinched cutting is used per pot.

It is claimed:

1. A new and distinct Kalanchoë plant named Isabella, as described and illustrated.

* * * * *